United States Patent [19]
Archibald et al.

[11] Patent Number: 5,450,852
[45] Date of Patent: Sep. 19, 1995

[54] CONTINUOUS NON-INVASIVE BLOOD PRESSURE MONITORING SYSTEM

[75] Inventors: G. Kent Archibald, Vadnais Heights; Timothy G. Curran, Ramsey; Orland H. Danielson, Roseville; Marius O. Poliac, St. Paul; Roger C. Thede, Minneapolis, all of Minn.

[73] Assignee: Medwave, Inc., St. Paul, Minn.

[21] Appl. No.: 227,506

[22] Filed: Apr. 14, 1994

Related U.S. Application Data

[63] Continuation-in-part of Ser. No. 150,382, Nov. 9, 1993.

[51] Int. Cl.$^6$ ............................................. A61B 5/021
[52] U.S. Cl. ..................................... 128/672; 128/687
[58] Field of Search ................ 128/672, 677, 687–690, 128/678–683

[56] References Cited

U.S. PATENT DOCUMENTS

| | | | |
|---|---|---|---|
| 4,260,951 | 4/1981 | Lewyn | 128/690 |
| 4,664,126 | 5/1987 | Link | |
| 4,699,151 | 10/1987 | Link | |
| 4,712,563 | 12/1987 | Link | |
| 4,799,491 | 1/1989 | Eckerle | |
| 4,928,702 | 5/1990 | Cousin | 128/678 |
| 5,025,792 | 6/1991 | Hon et al. | 128/690 |
| 5,033,471 | 7/1991 | Yokoe et al. | 128/681 |
| 5,238,000 | 8/1993 | Niwa | 128/690 |
| 5,247,944 | 9/1993 | Hirano et al. | 128/687 |
| 5,284,150 | 2/1994 | Butterfield et al. | 128/687 |

Primary Examiner—Angela D. Sykes
Attorney, Agent, or Firm—Kinney & Lange

[57] ABSTRACT

A transducer having a sensing surface for sensing blood pressure within an underlying artery of a patient includes a transducer, a sidewall, a flexible diaphragm and a fluid coupling medium. The sidewall supports the transducer above the underlying artery. The flexible diaphragm is spaced from the sensing surface of the transducer. The fluid coupling medium is coupled between the sensing surface of the transducer and the flexible diaphragm and transmits blood pressure pulses within the underlying artery from the flexible diaphragm to the sensing surface of the transducer. The fluid coupling medium is isolated from the sidewall so that forces are not transmitted from the sidewall through the fluid coupling medium to the transducer.

21 Claims, 5 Drawing Sheets

CONTINUOUS NON-INVASIVE BLOOD PRESSURE MONITORING SYSTEM

REFERENCE TO COPENDING APPLICATION

This is a continuation-in-part of application Ser. No. 08/150,382, filed Nov. 9, 1993 entitled CONTINUOUS NON-INVASIVE BLOOD PRESSURE MONITORING SYSTEM, pending.

BACKGROUND OF THE INVENTION

The present invention relates to systems for measuring arterial blood pressure. In particular, the invention relates to a sensor assembly for measuring arterial blood pressure in a relatively continuous and non-invasive manner.

Blood pressure has been typically measured by one of four basic methods: invasive, oscillometric, auscultatory and tonometric. The invasive method, otherwise known as an arterial line (A-Line), involves insertion of a needle into the artery. A transducer connected by a fluid column is used to determine exact arterial pressure. With proper instrumentation, systolic, mean and diastolic pressure may be determined. This method is difficult to set up, is expensive and involves medical risks. Set up of the invasive or A-line method poses problems. Resonance often occurs and causes significant errors. Also, if a blood clot forms on the end of the catheter, or the end of the catheter is located against the arterial wall, a large error may result. To eliminate or reduce these errors, the set up must be adjusted frequently. A skilled medical practitioner is required to insert the needle into the artery. This contributes to the expense of this method. Medical complications are also possible, such as infection or nerve damage.

The other methods of measuring blood pressure are non-invasive. The oscillometric method measures the amplitude of pressure oscillations in an inflated cuff. The cuff is placed against a cooperating artery of the patient and thereafter pressurized to different levels. Mean pressure is determined by sweeping the cuff pressure and determining the mean cuff pressure at the instant the peak amplitude occurs. Systolic and diastolic pressure is determined by cuff pressure when the pressure oscillation is at some predetermined ratio of peak amplitude.

The auscultatory method also involves inflation of a cuff placed around a cooperating artery of the patient. Upon inflation of the cuff, the cuff is permitted to deflate. Systolic pressure is indicated when Korotkoff sounds begin to occur as the cuff is deflated. Diastolic pressure is indicated when the Korotkoff sounds become muffled or disappear. The auscultatory method can only be used to determine systolic and diastolic pressures.

Because both the oscillometric and the auscultatory methods require inflation of a cuff, performing frequent measurements is difficult. The frequency of measurement is limited by the time required to comfortably inflate the cuff and the time required to deflate the cuff as measurements are made. Because the cuff is inflated around a relatively large area surrounding the artery, inflation and deflation of the cuff is uncomfortable to the patient. As a result, the oscillometric and the auscultatory methods are not suitable for long periods of repetitive use.

Both the oscillometric and auscultatory methods lack accuracy and consistency for determining systolic and diastolic pressure values. The oscillometric method applies an arbitrary ratio to determine systolic and diastolic pressure values. Similarly, the auscultatory method requires a judgment to be made as to when the Korotkoff sounds start and when they stop. This detection is made when the Korotkoff sound is at its very lowest. As a result, the auscultatory method is subject to inaccuracies due to low signal-to-noise ratio.

The fourth method used to determine arterial blood pressure has been tonometry. The tonometric method typically involves a transducer including an array of pressure sensitive elements positioned over a superficial artery. Hold down forces are applied to the transducer so as to flatten the wall of the underlying artery without occluding the artery. The pressure sensitive elements in the array typically have at least one dimension smaller than the lumen of the underlying artery in which blood pressure is measured. The transducer is positioned such that at least one of the individual pressure sensitive elements is over at least a portion of the underlying artery. The output from one of the pressure sensitive elements is selected for monitoring blood pressure. The pressure measured by the selected pressure sensitive element is dependent upon the hold down pressure used to press the transducer against the skin of the patient. These tonometric systems measure a reference pressure directly from the wrist and correlate this with arterial pressure. However, if a patient moves, recalibration of the tonometric system is required because the system may experience a change in gains. Because the accuracy of these tonometric systems depends upon the accurate positioning of the individual pressure sensitive element over the underlying artery, placement of the transducer is critical. Consequently, placement of the transducer with these tonometric systems is time-consuming and prone to error.

The oscillometric, auscultatory and tonometric methods measure and detect blood pressure by sensing force or displacement caused by blood pressure pulses as the underlying artery is compressed or flattened. The blood pressure is sensed by measuring forces exerted by blood pressure pulses in a direction perpendicular to the underlying artery. However, with these methods, the blood pressure pulse also exerts forces parallel to the underlying artery as the blood pressure pulses cross the edges of the sensor which is pressed against the skin overlying the underlying artery of the patient. In particular, with the oscillometric and the auscultatory methods, parallel forces are exerted on the edges or sides of the cuff. With the tonometric method, parallel forces are exerted on the edges of the transducer. These parallel forces exerted upon the sensor by the blood pressure pulses create a pressure gradient across the pressure sensitive elements. This uneven pressure gradient creates at least two different pressures, one pressure at the edge of the pressure sensitive element and a second pressure directly beneath the pressure sensitive element. As a result, the oscillometric, auscultatory and tonometric methods produce inaccurate and inconsistent blood pressure measurements.

SUMMARY OF THE INVENTION

A transducer having a sensing surface for sensing blood pressure within an underlying artery of a patient includes a transducer, a sidewall, a flexible diaphragm and a fluid coupling medium. The sidewall supports the transducer above the underlying artery. The flexible diaphragm is spaced from the sensing surface of the transducer. The fluid coupling medium is coupled between the sensing surface of the transducer and the flexible diaphragm and transmits blood pressure pulses within the underlying artery from the flexible diaphragm to the sensing surface of the transducer. The fluid coupling medium is isolated from the sidewall so that forces are not transmitted from the sidewall through the fluid coupling medium to the transducer.

DETAILED DESCRIPTION OF THE PREFERRED EMBODIMENTS

Figure 1:
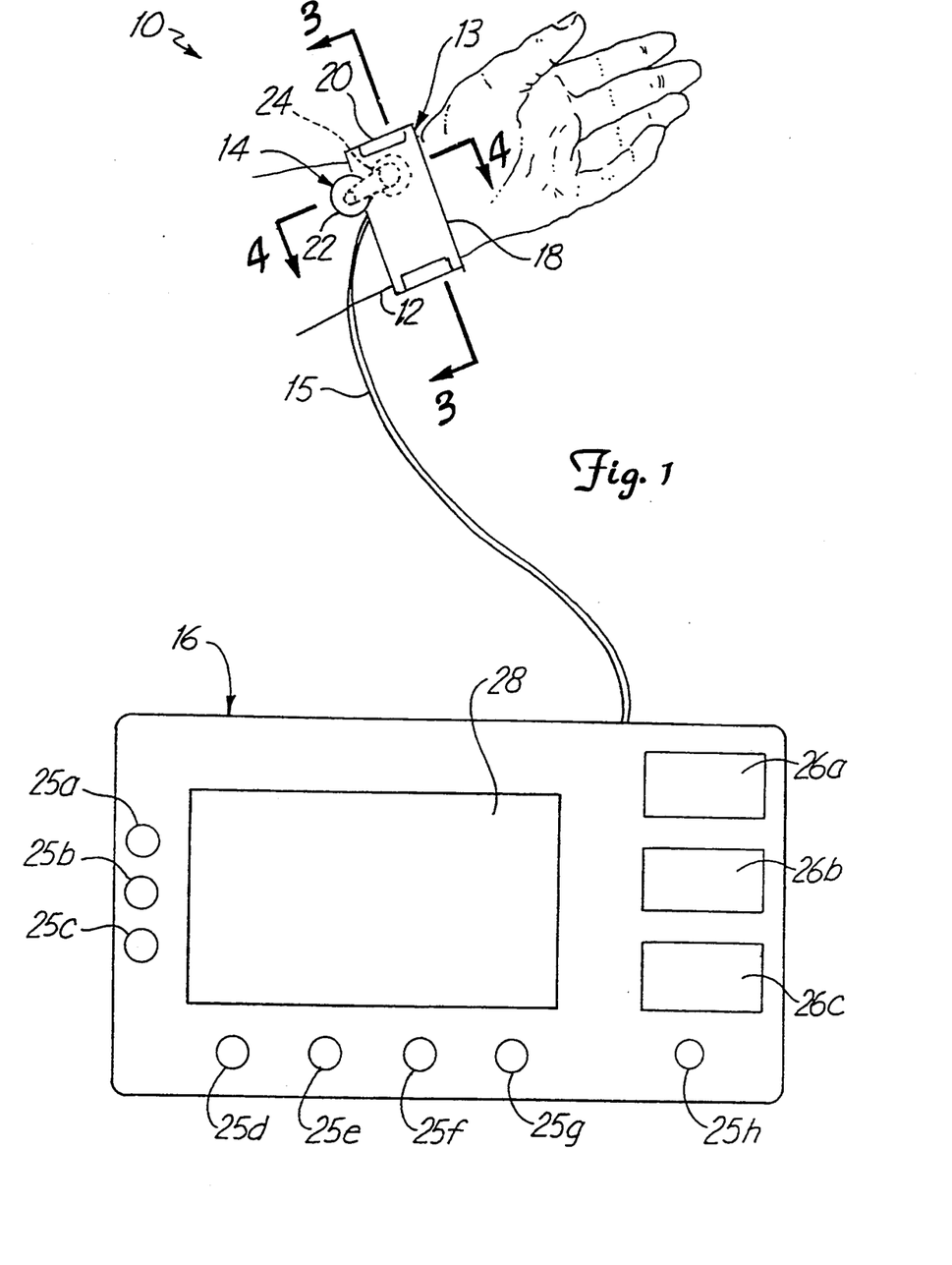
FIG. 1 is a perspective view of a blood pressure monitoring system having a sensor assembly mounted to the wrist of a patient.

FIG. 1 shows a blood pressure monitoring system 10 for measuring and displaying blood pressure within an underlying artery (not shown) within wrist 12 of a patient. Monitoring system 10 includes wrist assembly 13, sensor assembly 14, cable 15 and monitor 16.

Wrist assembly 13 includes sensor support 18 and strap 20. Sensor support 18 fits over wrist 12 above an underlying artery (not shown) and supports sensor assembly 14 over the underlying artery. Sensor support 18 is preferably rigid.

Strap 20 comprises a flexible band and is preferably made of nylon. Strap 20 latches to sensor support 18 and wraps around wrist 12 to maintain sensor assembly 14 on wrist 12.

Sensor assembly 14 is electrically coupled to monitor 16 through cable 15 and generally includes motor assembly 22 and sensor 24. Motor assembly 22 is coupled to sensor support 18 and is mechanically coupled to sensor 24. Motor assembly 22 applies a variable hold down pressure to sensor so that blood pressure can be sensed and measured as varying hold down pressures are applied to the underlying artery by sensor assembly 14.

Sensor 24 is coupled to motor assembly 22. When placed on wrist 12, sensor 24 is positioned over the underlying artery. Sensor 24 senses and measures blood pressure pulses within the underlying artery.

Monitor 16 is coupled to motor assembly 22 and to sensor 24 by cable 15. Monitor 16 includes control switches or various inputs 25a-25h, digital displays 26a-26c, and display screen 28. Inputs 25a-25h control monitor and permit monitor 16 to be calibrated. Inputs 25a-25c comprise hard keys for controlling monitor 16. Inputs 25d-25h consist of software programmable keys which are adaptable for various functions. Digital displays 26a-26c continually display systolic, diastolic and mean blood pressure, respectively. Display screen 28 displays the blood pressure pulse, waveforms and prompts to guide the operator. Monitor 16 receives the sensed blood pressure pulse signals taken by sensor 24 and calculates the systolic, diastolic and mean blood pressures. Once these values are determined, monitor 16 displays the corresponding values in both analog and digital form. Monitor 16 also controls motor assembly 22.

In operation, sensor 24 is strapped to wrist 12 over the radial artery. Motor assembly 22 moves sensor 24 to vary the pressure applied to wrist 12 above the radial artery. As this pressure is varied, an arterial pressure waveform is sensed. An arterial pressure waveform or shape is obtained by measuring amplitude of pressure versus time of an individual cardiac cycle. The shape of the waveform is a function of the applied pressure and is used by digital signal processing circuitry of monitor 16 to calculate systolic, mean and diastolic pressure. The calculated pressures are displayed by displays 26a-26c and display screen 28.

Figure 2:
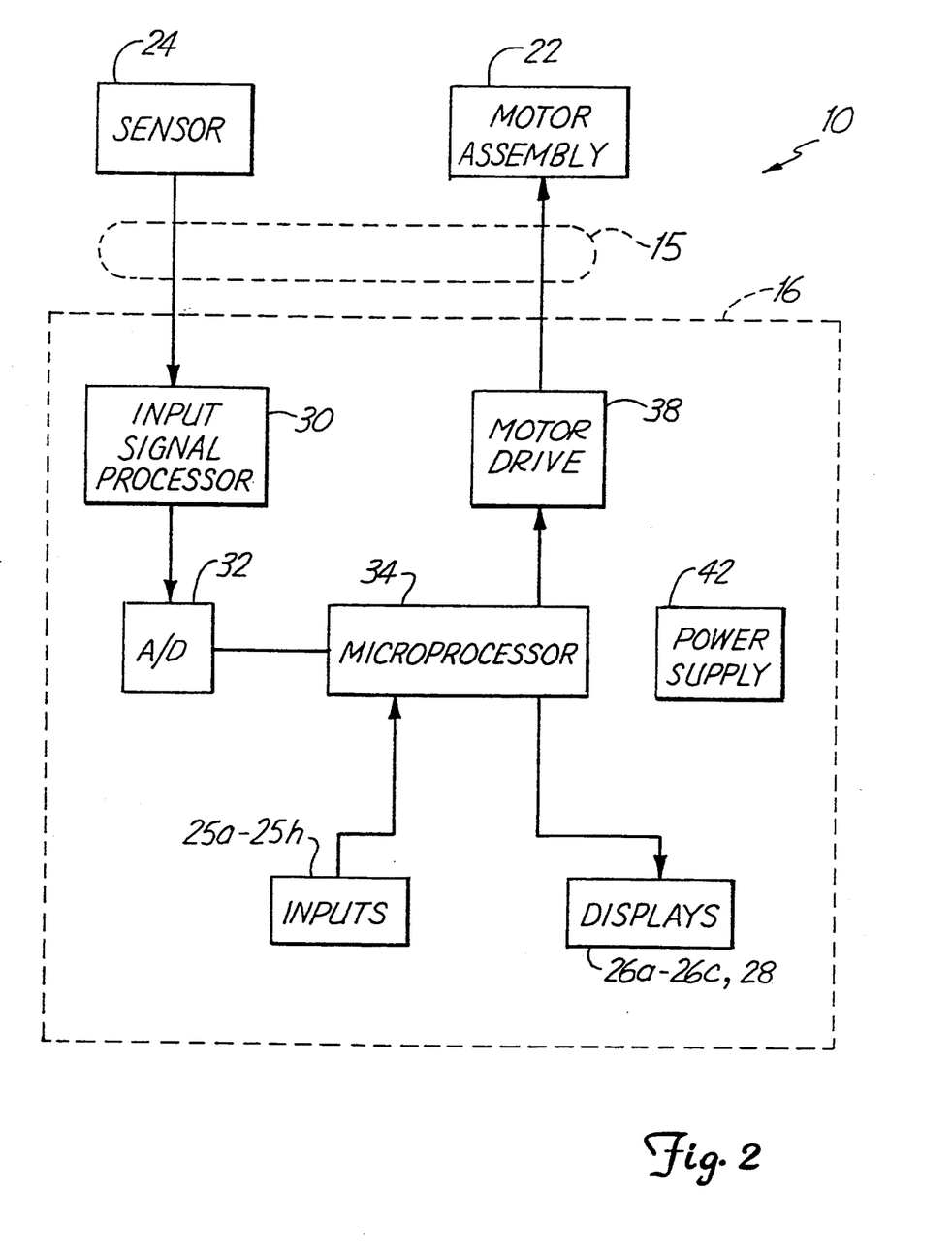
FIG. 2 is a block diagram of the blood pressure monitoring system of FIG. 1.

FIG. 2 shows a block diagram of blood pressure monitoring system 10. As best shown by FIG. 2, monitor 16 further includes input signal processor 30, analog-to-digital converter 32, microprocessor 34, inputs 25a-25h, motor drive 38, displays 26a-26c and 28, and power supply 42. In operation, microprocessor 34 receives inputted signals from inputs 25a-25h. Inputs 25a-25h may also consist of a keyboard or other input mechanisms. Inputs 25a-25h permit microprocessor 34 to be calibrated.

Microprocessor 34 controls motor drive 38 to vary hold down pressure applied by motor assembly 22 on sensor 24. Hold down pressure is applied to the anatomy of the patient directly above the artery by sensor 24. The hold down pressure applied by motor assembly 22 on sensor 24 is increased over time. As the force or hold down pressure applied by sensor 24 increases, the amplitude of the blood pressure pulse also increases until a maximum amplitude results. Once the maximum amplitude or maximum energy transfer results, the amplitude of the blood pressure pulse begins to decrease as the artery begins to flatten out beyond the point of maximum energy transfer.

Sensor 24 senses and detects the amplitude and shape of the blood pressure pulses within the underlying artery. Sensor 24 creates electric sensor signals representing the amplitude of the sensed blood pressure pulses. The sensor signals are transmitted to input signal processor 30 of monitor 16. Input signal processor 30 processes the sensor signals and filters any unwanted or undesirable noise and other effects. The sensor signals are then transmitted from input signal processor 30 to analog-to-digital convertor 32. Analog-to-digital convertor 32 converts the sensor signal into digital form. A digital signal representing the amplitude of the sensed blood pressure pulses is sent to microprocessor 34.

Based upon the digital sensor signals representing the sensed amplitude and shape of the blood pressure pulses, microprocessor 34 determines wave shape information by measuring amplitude and shape versus time of individual cardiac cycles. The arterial wave shape information is determined by sampling the arterial waves at a rate significantly above heart rate so that a good definition of the arterial pressure wave is measured. From this information, microprocessor 34 calculates systolic, diastolic and mean blood pressures. When no pressure gradient exists across the face of sensor 24, the hold down pressure corresponding to the cardiac cycle having the peak pressure amplitude or the maximum energy transfer is substantially equal to the mean arterial pressure. Based upon the mean arterial pressure, microprocessor 34 calculates systolic and diastolic blood pressure.

In the alternative, microprocessor 34 calculates blood pressure from the relationship between the pressure amplitude of the individual cardiac waveform and the applied hold down pressure of sensor 24. These results may be derived from waveforms both before and after the waveform that has maximum energy transfer.

In addition, microprocessor 34 may also calculate blood pressure from the shape of individual cardiac waveforms. These results are based on the area under part of the waveforms or they may be based on the shape of a rise time on any number of parameters. The calculated blood pressures are displayed on displays 26a-26c. Power supply 42 provides power to monitor 16 and motor assembly 22.

Figure 3:
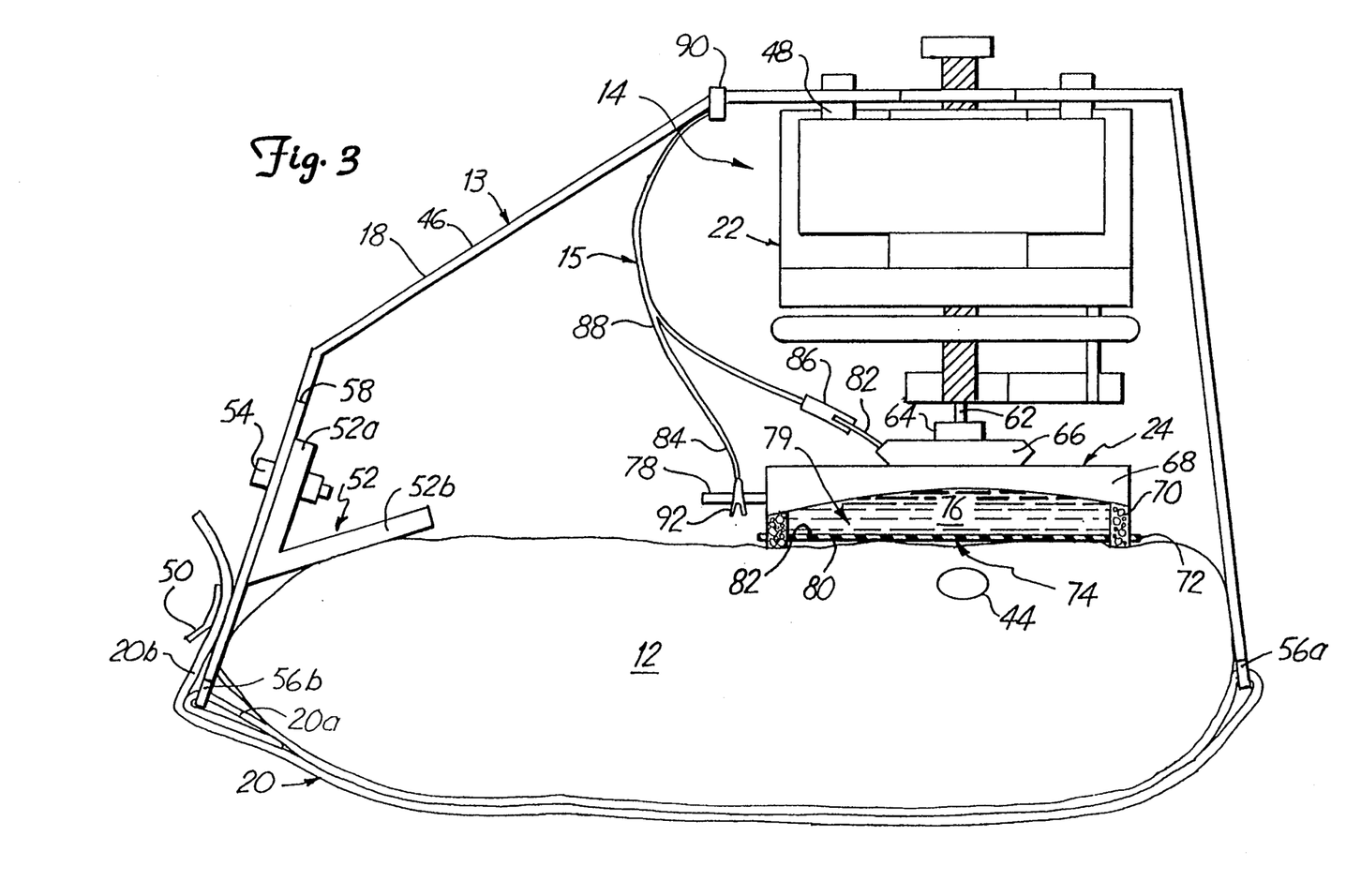
FIG. 3 is a cross-sectional view of the sensor assembly of FIG. 1 mounted to the wrist of the patient.

FIG. 3 is a cross-sectional view, taken along lines 3—3 of FIG. 1, showing wrist assembly 13 and sensor assembly 14 placed upon wrist 12 of a patient having an underlying artery 44. FIG. 3 shows sensor support 18 and strap 20 of wrist assembly 13 and sensor 24 of sensor assembly 14 in greater detail. Sensor support 18 includes frame 46, spacer 48, latch 50, stabilizing support 52 and screw 54. Frame 46 is a metal frame bent to partially surround wrist 12. Frame 46 includes lower strap holes 56a, 56b and adjustment slot 58. Strap holes 56a, 56b are located along the lower end of frame 46. Strap hole 56b permits end loop 20a of strap 20 to be secured to frame 46. Strap 20 is fed through strap hole 56a so that strap 20 is doubled back, and free end 20b is attached to latch 50. Adjustment slot 58 extends upward from above strap hole 56b toward a top end of frame 46. Adjustment slot 58 permits stabilizing support 52 to be moved up and down within slot 58 so that stabilizing support 52 may be adjusted for the particular anatomy to which sensor assembly 14 is being secured. Frame 46 supports motor assembly 22 and sensor 24 above underlying artery 44 of wrist 12. Frame 46 also supports strap 20 below wrist 12. As a result, sensor 24 is held in a stable position with respect to wrist 12 while blood pressure pulses are being sensed and measured.

Spacer 48 is mounted along a top horizontal portion of frame 46 and is positioned between sensor assembly 14 and frame 46. Spacer 48 spaces sensor assembly 14 from frame 46.

Latch 50 is fixedly coupled to frame 46 between strap hole 56b and adjustment slot 58. Latch 50 releasably secures free end 20b of strap 20 to frame 46 so that wrist 12 is supported and positioned between frame 46, sensor 24 and strap 20.

Stabilizing support 52 generally consists of a V-shaped bar having a first leg 52a extending parallel to adjustment slot 58 of frame 46 and having a second leg 52b extending over and above wrist 12. Stabilizing support 52 is slidably secured to frame 46 by screw 54. Screw 54 extends through first leg 52a and adjustment slot 58. Screw 54 and slot 58 cooperate to permit stabilizing support 52 to be vertically positioned with respect to wrist 12. Thus, second leg 52b of stabilizing support 52 holds wrist 12 down against strap 20 to limit movement of wrist 12 while blood pressure pulses within underlying artery 44 are being sensed and measured.

Strap 20 consists of an elongate flexible band. Strap 20 has a first end looped through strap hole 56b and secured to itself to form end loop 20a. Strap 20 has second free end 20b which is fed through strap hole 56a and doubled back below wrist 12 to latch 50 where free end 20b is latched and releasably secured to frame 46 by latch 50. Strap 20 supports wrist 12 in position below frame 46 and sensor 24.

Also as best shown by FIG. 3, sensor 24 is coupled to cable 15 and includes pivot block pin 62, pivot block 64, transducer 66, flange 68, sidewall 70, restraining ring 72, diaphragm 74, pressure or fluid coupling medium 76 and fluid gel port 78. Pivot block pin 62 has a first end coupled to pivot block 64 and a second end which is coupled to motor assembly 22. Pivot block pin 62 couples sensor 24 to motor assembly 22.

Pivot block 64 receives the first end of pivot block pin 62. Pivot block 64 has a lower end which is coupled to transducer 66. Pivot block 64 couples sensor 24 to motor assembly 22.

Transducer 66 is disc-shaped. Transducer 66 is coupled between pivot block 64 and flange 68. Transducer 66 contains a pressure-sensitive element such as a piezo-resistive sensor bridge (not shown) for sensing blood pressure pulses within artery 44.

Flange 68 is annular and is slightly concave so that sensor 24 better conforms to the anatomy or shape of wrist 12. Flange 68 is fixedly coupled around an outer perimeter of transducer 66. Flange 68 supports side wall 70 and couples side wall 70 to transducer 66.

Side wall 70 is ring shaped and compressible, and is coupled to a lower surface of flange 68. Side wall 70 is distant from transducer sensing elements (not shown) of transducer 66, yet engages tissue surrounding artery 44 to support transducer 66 above artery 44 and above tissue surrounding artery 44. As a result, the exact positioning of transducer 66 over artery 44 is not required. At the same time, side wall 70 is not so distant from transducer 66 so as to surround a large enough area of tissue surrounding artery 44 to cause discomfort to the patient. Because sidewall 70 separates transducer 66 from the tissue surrounding artery 44, blood pressure measurement errors caused by inadvertent patient movement are lessened.

In addition, sidewall 70 creates a substantially zero pressure gradient across sensor 24 so that sensor 24 more accurately measures blood pressure. Sidewall 70 is constrained from expanding outward in a planar direction away from the outer perimeter of transducer 66. Because side wall 70 is compressible, side wall 70 dampens and absorbs forces or pressure exerted by blood pressure pulses as the pulses cross side wall 70 along the perimeter or edge of sensor 24. Side wall 70 also applies force to tissue surrounding artery 44. The force applied by side wall 70 substantially equals force exerted by the tissue surrounding artery 44 to offset or neutralize the force exerted from the tissue. As a result, the force applied by side wall 70 presses the tissue to a neutral position so the pressure of artery 44 can be more accurately measured. The force of side wall 70 that is applied to the tissue surrounding artery 44 is coupled to flange 68. Flange 68 is coupled to transducer 66, but is not coupled to transducer sensing elements (not shown) of transducer 66. Thus, the force applied by side wall 70 which is used to press the tissue to a neutral position is not sensed by the transducer sensing elements of transducer 66. This neutralizing effect of sensor 24 allows blood pressure monitoring system 10 to more accurately measure the arterial pressure of artery 44 without inaccuracies introduced by forces from the surrounding tissue. Consequently, side wall 70 reduces or eliminates uneven pressure gradients within fluid coupling medium 76 across sensor 24 to create a substantially zero pressure gradient across sensor 24. As a result, sensor 24 more consistently and more accurately measures blood pressure. Preferably, side wall 70 is formed from closed cell foam. Alternatively, side wall 70 may be formed from open cell foam or other compressible materials or structural designs.

Because side wall 70 is compressible, side wall 70 better conforms to the anatomy or shape of wrist 12. However, because side wall 70 is constrained from expanding outward, side wall 70 does not stretch diaphragm 74 when being pressed against wrist 12. By preventing tension across diaphragm 74, sensor 24 further eliminates pressure gradients across transducer 66, which results in more accurate and consistent blood pressure readings.

Restraining ring 72 normally consists of a flexible ring made of fiber or other similar material. Restraining ring 72 encircles side wall 70 and further prevents side wall 70 from expanding outward in a direction away from the outer perimeter of transducer 66.

Diaphragm 74 is preferably formed from a thin flexible polymer or rubber. Diaphragm 74 extends across side wall 70 to form chamber 79 in front of transducer 66. Diaphragm 74 is preferably positioned across side wall 70 so as to be free of tension. Diaphragm 74 transmits blood pressure pulses from a first side 80 to a second side 82 within chamber 79.

Fluid coupling medium 76 preferably is a gel, although fluid coupling medium 76 may consist of any fluid or liquid capable of transmitting pressure from diaphragm 74 to transducer 66. Fluid coupling medium 76 is contained within chamber 79 between diaphragm 74, side wall 70, flange 68 and transducer 66. Fluid coupling medium 76 interfaces between diaphragm 74 and transducer 66 and transmits the blood pressure pulses from surface 82 of diaphragm 74 to transducer 66.

Sensor 24 continuously and accurately senses blood pressure pulses within the underlying artery. Because sidewall 70 is compressible, sensor 24 dampens forces parallel to the underlying artery which are extended upon sensor 24 by blood pressure pulses crossing beneath the edge of sensor 24. In addition, sensor 24 better conforms to the anatomy of wrist 12. Because sidewall 70 and diaphragm 74 are constrained from expanding outward and are free of tension, pressure gradients across transducer 66 are eliminated. Moreover, sensor 24 also neutralizes the tissue surrounding artery 44. Consequently, more accurate and consistent blood pressure readings are taken. Moreover, sidewall 70, diaphragm 74 and fluid coupling medium 76 form a large sensing area through which blood pressure pulses may be transmitted to transducer 66. As a result, sensor 24 is not as dependent upon accurate positioning of transducer 66 over the underlying artery. Sensor 24 quickly and accurately provides a continuous measurement of blood pressure over long periods of use without discomfort to the patient.

Fluid port 78 extends into flange 68 and communicates with chamber 79. Port 78 permits chamber 79 to be filled with fluid coupling medium 76.

Cable 15 electrically couples sensor 24 to the monitor 16. Cable 15 includes transducer leads 82, ground wire 84, connector 86, cable 88 and clamp 90. Transducer leads 82 consist of wires electrically coupled to transducer 66. Transducer leads 82 transmit signals representing the sensed blood pressure pulses from transducer 66.

Grounding wire 84 consists of a wire having a grounding clip 92 at one end. Grounding clip 92 mounts onto fluid port 78. An opposite end of grounding wire 84 is electrically coupled to cable 88. Grounding wire 84 electrically grounds sensor assembly 24.

Connector 86 electrically couples transducer leads 82 to cable 88. Cable 88 has first end coupled to connector 88 and a second end which is coupled to monitor 16 (shown in FIG. 1). Cable 88 permits sensor 24 to transmit signals representing the sensed blood pressure pulses to monitor 16 where the signals are measured. Clamp 90 couples cable 88 to frame 46 of sensor support 18 and relieves strain within cable 88.

Figure 4:
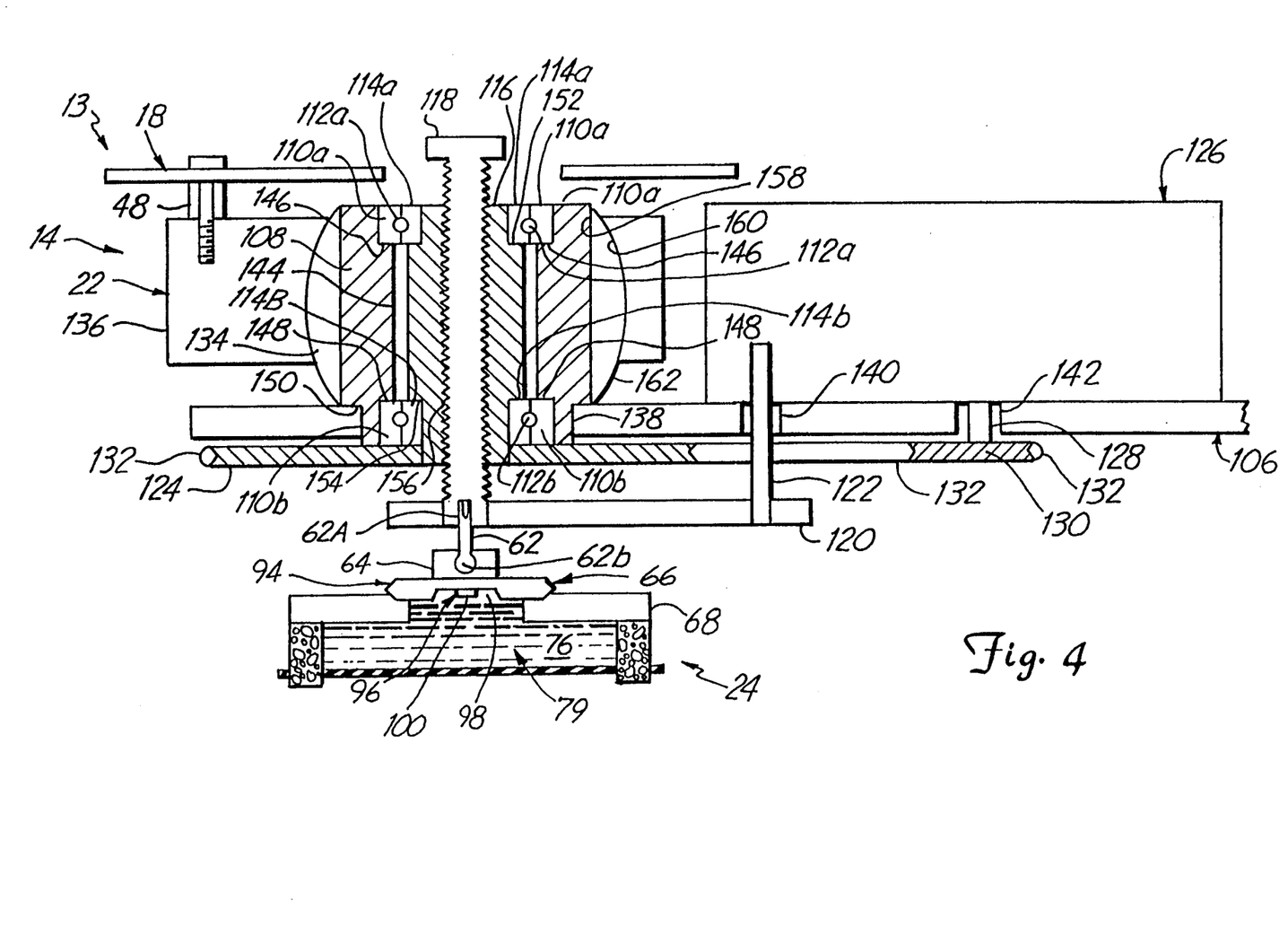
FIG. 4 is a cross-sectional view of the sensor assembly of FIG. 1 having a sensor.

FIG. 4 is a cross-sectional view of sensor assembly 14 and sensor support 18 of wrist assembly 13 taken along lines 4—4 of FIG. 1. FIG. 4 shows sensor 24 and motor assembly 22 in greater detail. Portions of sensor support 18 are omitted for clarity. FIG. 4 best shows pivot block pin 62 and pivot block 64 of sensor 24. As shown in FIG. 4, upper end 62a of pivot block pin 62 is bifurcated and is frictionally coupled to motor assembly 22. Because pivot block pin 62 is bifurcated, the diameter of pivot block pin 62 may be enlarged or reduced. As a result, pivot block pin 62 and sensor 24 may be removed from motor assembly 22 without the use of tools by compressing pivot block pin 62 to reduce its diameter. Pivot block 64 includes a cavity for receiving the lower end 62b of pivot block pin 62. Pivot block 64 rotates or pivots about lower end 62b of pivot block pin 62 to permit accurate orientation of sensor 24.

As best shown by FIG. 4, transducer 66 is generally disc-shaped and includes transducer holder 94 and transducer element 96. Transducer holder 94 includes central bore 98 extending into a lower end of transducer holder 94. Transducer holder 94 has a top end which is coupled to pivot block 64. The lower end of transducer holder 94 is fixedly secured to flange 68. Transducer element 96 is supported and mounted within bore 98 of transducer holder 94.

Transducer element 96 is well known in the art and includes sensing surface 100. Sensing surface 100 is preferably sensitive to pressure changes within chamber 79 transmitted through fluid coupling medium 76. Transducer element 96 is positioned within bore 98 of transducer holder 94 so that sensing surface 100 of transducer element 96 faces downward out of bore 98. Transducer element 96 preferably comprises a piezoresistive sensor bridge. Transducer element 96 senses blood pressure pulses from an underlying artery of a patient.

Motor assembly 22 presses sensor 24 against skin overlying the underlying artery so that the amplitudes of blood pressure pulses may be sensed over a range of various hold down pressures. As best shown by FIG. 4, motor assembly 22 includes base plate 106, outer sleeve 108, upper and lower outer races 110a and 110b, bearing balls 112a and 112b, upper and lower inner races 114a and 114b, inner sleeve 116, threaded screw shaft 118, stop arm 120, stop shaft 122, drive pulley 124, motor 126, drive shaft 128, motor pulley 130, drive belt 132, ball 134 and socket 136.

Base plate 106 is an elongate flat rigid plate which includes sleeve hole 138, stop shaft hole 140 and drive shaft hole 142. Sleeve hole 138 has a diameter large enough to permit outer sleeve 108, inner sleeve 116 and screw shaft 118 to extend through sleeve hole 138. Stop shaft hole 140 has a diameter large enough to permit stop shaft 122 to extend through stop shaft hole 140.

Drive shaft hole 142 permits drive shaft 128 to couple motor 126 to motor pulley 130.

Outer sleeve 108 is generally cylindrical and includes bore 144, upper inside shoulder 146, lower inside shoulder 148, and lower outside shoulder 150. Bore 144 extends through outer sleeve 108. Towards a top end and a bottom end of outer sleeve 108, bore 144 widens to form upper inside shoulder 146 and lower inside shoulder 148, respectively. Toward a lower end of outer sleeve 108, an outer diameter of sleeve 108 narrows to form lower outside shoulder 150. Lower outside shoulder 150 engages sleeve hole 138 of base plate 106 and fixedly couples outer sleeve 108 to base plate 106. Upper inside shoulder 146 and lower inside shoulder 148 support outer races 110. Inside races 114 are coupled to inner sleeve 116. Inner races 110 and outer races 114 cooperate to support an annular array of bearing balls 112 therebetween. As a result, outer sleeve 108 rotatably supports inner sleeve 116.

Inner sleeve 116 is cylindrical in shape and includes upper outside shoulder 152, lower outside shoulder 154 and threaded inner bore 156. Towards an upper end and a lower end of inner sleeve 116, an outer diameter narrows to form upper outside shoulder 152 and lower outside shoulder 154, respectively. Shoulders 152 and 154 support inner races 114a and 114b, respectively. Threaded inner bore 156 extends through inner sleeve 156 and receives threaded screw shaft 118.

Threaded screw shaft 118 extends through threaded bore 156 of inner sleeve 116. The lower end of threaded screw shaft 118 receives an upper end of pivot block pin 62. Consequently, threaded screw shaft 118 is coupled to and supports sensor 24. Threaded screw shaft 118 is further coupled to stop arm 120.

Stop arm 120 generally consists of an elongate arm having a first end fixedly coupled to a lower end of threaded screw shaft 118 and having a second end fixedly coupled to a lower end of stop shaft 122. Stop shaft 122 extends upward from stop arm 120 through stop shaft hole 140 of base plate 106. Stop arm 120 and stop shaft 122 prevent threaded screw shaft 118 from rotating. At the same, stop arm 120 and stop shaft 122 permit threaded screw shaft 118 to move up and down. As a result, rotation of inner sleeve 116 with respect to threaded screw shaft 118 causes threaded screw shaft 118 to move up and down as the threads of threaded screw shaft 118 engage the threads of inner sleeve 116. Because sensor 24 is coupled to threaded screw shaft 118, movement of threaded screw shaft 118 up and down causes sensor 24 to vary pressure applied to skin above the underlying artery. As pressure is varied, an arterial pressure waveform is generated which is measured by transducer 66 of sensor 24.

Drive pulley 124 generally consists of a circular pulley. Drive pulley 124 has a groove along its outer perimeter sized to accommodate drive belt 132. Drive pulley 124 is fixedly secured to a lower end of inner sleeve 116 below base plate 106. Rotation of drive pulley 124 permits inner sleeve 116 to be rotated so that threaded screw shaft 118 is raised and lowered.

Motor 126 is fixedly coupled to base plate 106. Motor 126 drives drive shaft 128. Drive shaft 128 extends through drive shaft hole 142 and is coupled to motor pulley 130 below base plate 106. Motor pulley 130 is circular and has an outer groove along its perimeter sized to accommodate drive belt 132. Drive belt 132 generally consists of a band or belt. Drive belt 132 fits within the grooves of drive pulley 124 and motor pulley 130. Drive belt 132 partially encircles drive pulley 124 and motor pulley 130 to provide rotational communication between drive pulley 124 and motor pulley 130.

In operation, motor 126 rotates motor pulley 130, which in turn, rotates drive pulley 124 and inner sleeve 116. As a result, rotation of motor pulley 130 by motor 126 causes threaded screw shaft 118 to move up and down depending upon the rotational direction of motor pulley 130 and inner sleeve 116. By raising and lowering screw shaft 118 and sensor 24, motor 126 controls and continuously varies the hold down pressure applied to the skin above the underlying artery by sensor 24. This interaction between sensor 24 and the underlying artery permits blood pressure monitoring system 10 to better measure blood pressure.

Ball 134 includes central bore 158 and convex surface 160. Central bore 158 extends from a top end to a bottom end of ball 134. Central bore 158 permits outer sleeve 108 to be press-fit within ball 134. Convex surface 160 frictionally engages socket 136 to hold sensor assembly 14 in position. Convex surface 160 of ball 134 also permits sensor assembly 14 to be oriented in a proper position for accurate operation.

Socket 136 is generally rectangular and is coupled to frame 46 of sensor support 18. Socket 136 includes concave bore 162. Concave bore 162 engages convex surface 160 of ball 134 to guide the positioning of ball 134 within socket 136 so that sensor assembly 14 may be properly oriented during operation.

Sensor 24 provides continuous external measurements of blood pressure in an underlying artery. Because sensor 24 calculates blood pressure non-invasively, blood pressure is measured at a lower cost and without medical risks. In addition, sensor 24 provides continuous measurements of blood pressure. Because sensor 24 is relatively small compared to the larger cuffs used with the oscillometric and auscultatory methods, sensor 24 applies a hold down pressure to only a relatively small area above the underlying artery of the patient. Consequently, blood pressure measurements may be taken with less discomfort to the patient. Because sensor 24 does not require inflation or deflation, continuous, more frequent measurements may be taken. At the same time, sensor 24 permits accurate and consistent calculation of blood pressure. Because the side wall, diaphragm and fluid coupling medium of sensor 24 forms a large sensing area through which blood pressure pulses may be transmitted to transducer 66, sensor 24 is not as dependent upon accurate positioning of transducer 66 over the underlying artery. Thus, sensor 24 is more tolerant to patient movement as measurements are being taken. Moreover, because the side wall of sensor 24 dampens and absorbs forces from the blood pressure pulses which are parallel to the underlying artery, uneven pressure gradients across transducer 66 are eliminated. The side wall of sensor 24 also presses tissue surrounding the artery to neutralize or offset forces exerted by the tissue. Consequently, sensor 24 senses blood pressure more consistently and more accurately.

Figure 5:
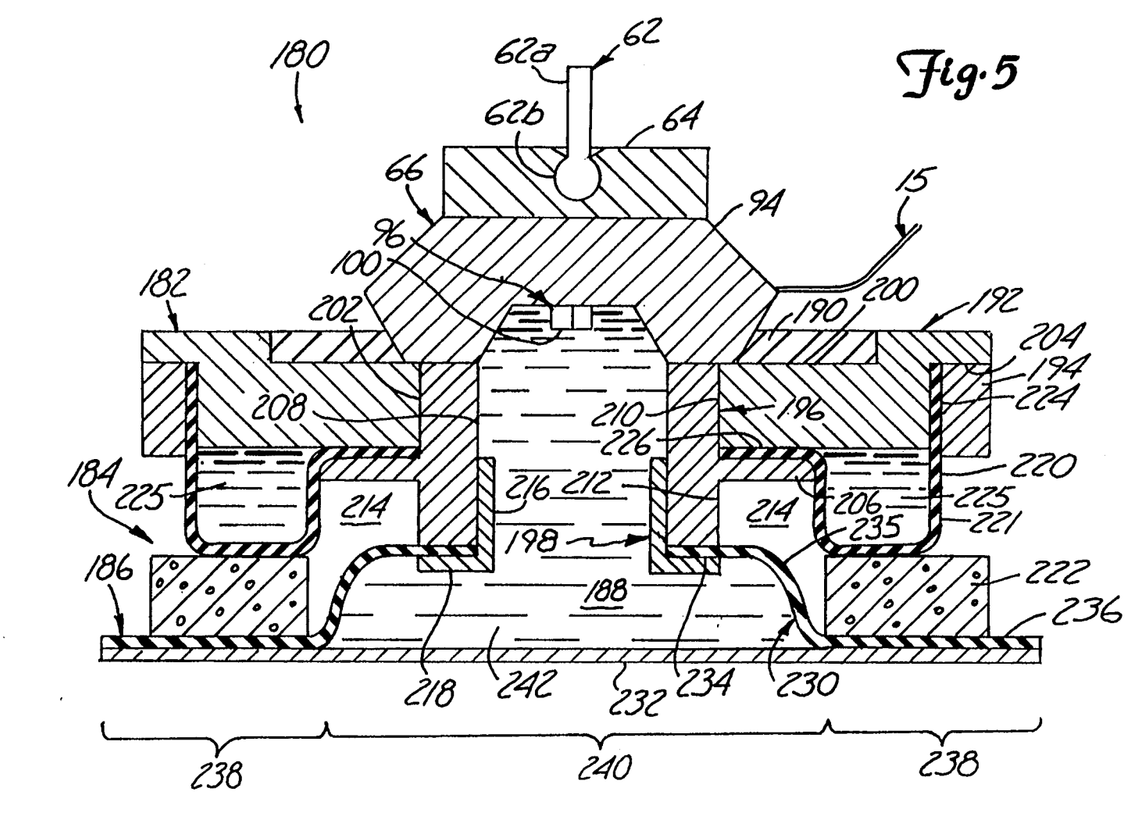
FIG. 5 is a cross-sectional view of an alternate embodiment of the sensor of FIG. 4.

FIG. 5 shows a cross-sectional view of an alternate embodiment (sensor 180) to sensor 24 shown in FIG. 4. For sake of illustration, those elements of sensor 180 which are the same as those elements of sensor 24 are numbered similarly. Sensor 180 includes transducer 66, flange 182, sidewall 184, diaphragm 186 and fluid coupling medium 188. As discussed above, transducer 66 is mounted to pivot block pin 62 and includes transducer holder 94 and transducer element 96. Transducer holder 94 is coupled to flange 182 and supports transducer element 96.

Transducer element 96 is well known in the art and includes sensing surface 100. Sensing surface 100 is sensitive to pressure changes transmitted through fluid coupling medium 188. Transducer element 96 preferably comprises a piezoresistive sensor bridge. Transducer element 96 senses blood pressure pulses from an underlying artery of a patient and transmits the sensed blood pressure pulses through cable 15 to monitor 16 (not shown) for measurement and analysis.

Flange 182 is coupled between transducer 66 and sidewall 184 and includes plate 190, top 192, outer ring 194, upper insert 196 and lower insert 198. Plate 190 generally consists of a flat annular collar. Plate 190 is fixedly secured around the lower portion of transducer holder 94 of transducer 66. Plate 190 provides a supporting area for mounting transducer 66 to top 192.

Top 192 is a generally flat annular platform, base or stand and includes depression 200, bore 202, and shoulder 204. Depression 200 extends into an upper surface of top 192 and preferably has a shape nearly identical to the shape of plate 190. Depression 200 permits plate 190 and transducer 66 to be securely fixed to and centered on top 192.

Bore 202 extends from a lower surface of top 192 to the upper surface of top 192. Bore 202 is preferably coaxially centered about sensing surface 100 of transducer element 96. Bore 202 has a diameter sized for the reception of upper insert 196.

Shoulder 204 is defined by outward extending ends extending along an outer perimeter of top 192 near the upper surface. Shoulder 204 and the outer perimeter of top 204 are sized for receiving and engaging outer ring 194. Shoulder 196 limits accidental upward movement of outer ring 194 and provides an additional surface for securely mounting outer ring 194.

Outer ring 194 generally consists of a circular ring having an inner diameter large enough to receive top 192 below shoulder 204. Ring 194 engages the outer perimeter of top 192 below shoulder 204 to partially support sidewall 184 captured therebetween. Outer ring 194 is preferably fixed to top 192 and sidewall 184 by adhesive. Alternatively, outer ring 194 may be press fit around top 192 and sidewall 184.

Upper insert 196 is a generally cylindrical shaped member including step or spar 206 and bore 208. An outer surface or perimeter of insert 196 projects outwardly to form spar 206. Spar 206 engages the lower surface of top 192 to partially support sidewall 184 which is partially captured between top 192 and spar 206. In the preferred embodiment, adhesive is used between the lower surface of top 192 and spar 206 to fixedly secure the portion of sidewall 184 trapped therebetween. Alternatively, spar 206 may be press fit against the lower surface of top 192 to secure and support sidewall 184. Spar 206 further divides the outer perimeter of insert 196 into two portions, an upper portion 210 and a lower portion 212. Upper portion 210 fits within bore 202 of top 192. Upper portion 210 preferably has a height approximately equal to the thickness of top 192 between the lower surface of top 192 and depression 200 so that insert 196 engages the lower surface of transducer holder 94. Upper portion 210 is preferably adhesively secured to top 192 within bore 202. Lower portion 212 extends below spar 206. Lower portion 212, spar 206 and sidewall 184 define expansion cavity 214.

Expansion cavity 214 enables diaphragm 186 to initially change shape while only experiencing a small change in volume.

Bore 208 extends through insert 196 and partially contains fluid coupling medium 188. Bore 208 has a diameter sized for the reception of lower insert 198.

Lower insert 198 is a thin, elongated, annular ring including bore 216 and lower lip 218. Bore 216 extends through lower insert 198 and partially contains fluid coupling medium 188. Lip 218 projects outwardly from a lower end of insert 198. Lower insert 198 fits within bore 208 of upper insert 196 until lip 218 engages a lower rim of upper insert 196. Lower insert 198 is preferably adhesively affixed to upper insert 198. Alternatively, lower insert 198 may be press fit within upper insert 196. Lip 218 of lower insert 196 engages upper insert 196 to support diaphragm 186 between lip 218 and insert 196.

Flange 182 serves as a base or supporting structure upon which transducer 66, sidewall 184 and diaphragm 186 are affixed. Because plate 190, top 192, outer ring 194, upper insert 196, and lower insert 198 of flange 182 all engage and fit within one another to mount transducer 66, sidewall 184 and diaphragm 186, flange 182 permits sensor 180 to be easily manufactured and assembled at a lower cost and in less time.

Sidewall 184 supports and spaces transducer 66 above the underlying artery and includes top sidewall or ring 220 and bottom sidewall or ring 222. Top ring 220 generally consists of annular compressible ring coupled between top 192 of flange 182 and bottom ring 222. Ring 220 is preferably formed from a generally circular sheet 221 of flexible material, such as vinyl, and is partially filled with fluid 225. Sheet 221 has a hole sized to fit around upper portion 210 of upper insert 196. Sheet 221 includes outer edge portion 224 and inner edge portion 226. Outer edge portion 224 is trapped and held between outer ring 194 and top 192. Inner edge portion 226 is trapped and supported between top 192 and spar 206 of upper insert 196. As a result, ring 220 forms a continuous annular chamber which is partially filled with fluid 225. Because ring 220 is formed from a flexible material and is only partially filled with fluid 225, top ring 220 is compressible so as to be able to conform to the anatomy of the patient surrounding the underlying artery. As a result, the distance between top 192 and the patient's anatomy can vary around the periphery of sidewall 184 according to the contour of the patient's anatomy. Furthermore, because fluid 225 is permitted to flow through and around ring 220, pressure around ring 220 is equalized around the patient's anatomy.

Bottom sidewall or ring 222 generally consists of an annular compressible ring and is preferably formed from a foam rubber or other pulse dampening material such as open celled foam or closed cell foam. Ring 222 is centered about and positioned between top ring 220 and diaphragm 186. Ring 222 is isolated from fluid coupling medium 188. Because ring 222 is formed from a compressible material, ring 222 absorbs and dampens forces in a direction parallel to the underlying artery which are exerted by the blood pressure pulses on sensor 180 as the blood pressure pulse crosses sensor 180. Because bottom ring 222 is isolated from fluid coupling medium 188, the forces absorbed or received by ring 222 cannot be transmitted to the fluid coupling medium 188. Instead, these forces are transmitted across ring 222 and ring 220 to top 192. Because this path is distinct and separate from fluid coupling medium 188, fluid coupling medium 188 is isolated from these forces. In addition, bottom ring 222 also presses tissue surrounding the artery to neutralize or offset forces exerted by the tissue.

Diaphragm 186 is a generally flat surfaced sac preferably formed from upper diaphragm sheet 230 and lower diaphragm sheet 232. Upper diaphragm sheet 230 is an annular sheet of flexible material having an inner portion 234, an intermediate portion 235, an outer portion 236 and an inner diameter sized to fit around lower insert 198. Inner portion 234 is trapped or captured between lip 218 of lower insert 198 and the bottom rim of upper insert 196 to support diaphragm 186 from flange 182. Inner portion 234 is preferably adhesively affixed between lip 218 and upper insert 196.

Intermediate portion 235 lies between inner portion 234 and outer portion 236. Intermediate portion 235 is adjacent to expansion cavity 214 and is isolated from rings 220 and 222 of sidewall 184. Because intermediate portion 235 is positioned adjacent to expansion cavity 214, intermediate portion 235 is permitted to initially move upward into expansion cavity 214 as sidewall 184 and diaphragm 186 conform to the anatomy of the patient surrounding the underlying artery while the cavity containing fluid coupling medium 188 experiences only a small change in volume. As bottom ring 222 is pressed against the anatomy of the patient surrounding the artery to neutralize or offset forces exerted by the tissue, diaphragm 186 is also compressed. However, because intermediate portion 235 is permitted to roll into expansion cavity 214, the cavity containing fluid coupling medium 188 does not experience a large volume decrease and a large corresponding pressure increase. Thus, sensor 180 permits greater force to be applied to the anatomy of the patient through sidewall 184 to neutralize tissue surrounding the artery without causing a corresponding large change in pressure within the cavity containing fluid coupling medium 188 as the height of sidewall 184 changes. As a result, sensor 180 achieves more consistant and accurate blood pressure measurements.

Outer portion 236 is the outer most edge of upper diaphragm sheet 230. Outer portion 236 extends within and outwardly beyond ring 222 of sidewall 184. Outer portion 236 is preferably not bonded or coupled to a lower surface of ring 222. Outer portion 236 of upper diaphragm sheet 230 is bonded to lower diaphragm sheet 232 at a distance within the inner diameter of ring 222 of sidewall 184 so that intermediate portion 235 does not contact ring 222 of sidewall 184. To further prevent intermediate portion 235 from contacting ring 222, intermediate portion 235 is preferably made of a flexible material having sufficient rigidity to prevent intermediate portion 235 from bowing outwardly and contacting ring 222.

Lower diaphragm sheet 232 is a generally circular sheet of flexible material capable of transmitting forces from an outer surface to an inner surface of sheet 232. Sheet 232 is coupled to upper diaphragm sheet 230 and is configured for being positioned over the anatomy of the patient above the underlying artery. Lower diaphragm sheet 232 includes non-active portion or skirt 238 and active portion 240. Skirt 238 constitutes the area of sheet 232 where upper diaphragm sheet 230, namely outer portion 236, is bonded to lower diaphragm sheet 232. Because skirt 238 and outer portion 236 are generally two bonded sheets of flexible material, forces parallel to the underlying artery are transmitted across skirt 238 and outer portion 236 and are dampened by the compressible material of ring 222. In addition, because skirt 238 and outer portion 236 preferably extend outward beyond ring 222 of sidewall 184 and are not fixedly secured to ring 222, skirt 238, outer portion 236 and active portion 240 are permitted to bow inwardly to better conform to the anatomy of the patient surrounding the underlying artery.

Active portion 240 is constituted by the portion of lower diaphragm sheet 232 which is not bonded to upper diaphragm sheet 230. Active portion 240 is positioned below and within the inner diameter of ring 222 of sidewall 184. Active portion 240 of diaphragm 186 is the active area of sensor 180 which receives and transmits pulse pressure to transducer 66. Active portion 240 of diaphragm 186, intermediate portion 235 of upper diaphragm sheet 230, bore 216 of lower insert 198 and bore 208 of upper insert 196 define interface chamber 242.

Interface chamber 242 is an elongated fluid passage or cavity extending from active portion 240 of diaphragm 186 through bores 208 and 216 to sensing surface 100 of transducer element 96. Interface chamber 242 is isolated from sidewall 184. Interface chamber 242 contains fluid coupling medium 188.

Fluid coupling medium 188 is preferably a gel, although fluid coupling medium 188 may consist of any fluid or liquid capable of transmitting pressure from diaphragm 186 to transducer 66. Fluid coupling medium 188 interfaces between active portion 240 of diaphragm 186 and transducer 66 and transmits blood pressure pulses from active portion 240 to sensing surface 100 of transducer element 96. Because fluid coupling medium 188 is contained within interface chamber 242 which is isolated from sidewall 184, fluid coupling medium 188 does not transmit blood pressure pulses parallel to the underlying artery, forces from the tissue surrounding the underlying artery and other forces absorbed by sidewall 184 to transducer 66. As a result, sensor 180 more accurately measures and detects arterial blood pressure.

As with sensor 24, sensor 180 provides continuous external measurements of blood pressure in an underlying artery. Because sensor 180 calculates blood pressure non-invasively, blood pressure is measured at a lower cost and without medical risks. In addition, sensor 180 provides continuous measurements of blood pressure. Because sensor 180 is relatively small compared to the larger cuffs used with oscillometric and auscultatory methods, sensor 180 applies a hold down pressure to only a relatively small area above the underlying artery of the patient. Consequently, blood pressure measurements may be taken with less discomfort to the patient. Because sensor 180 does not require inflation or deflation, continuous, more frequent measurements may be taken.

Furthermore, sensor 180 better conforms to the anatomy of the patient so as to be more comfortable to the patient and so as to achieve more consistent and accurate blood pressure measurements. Because ring 220 is compressible and is partially filled with fluid, ring 220 better conforms to the anatomy of the patient and equalizes pressure applied around ring 220 to the patient's anatomy. Because bottom ring 222 is compressible and because diaphragm 186 is flexible and is permitted to bow or deform inwardly, bottom ring 222 and diaphragm 186 also better conform to the anatomy of the patient. At the same time, however, sensor 180 does not experience a large sudden increase in pressure in interface chamber 242 as bottom ring 222 and diaphragm 186 are pressed against the anatomy of the patient. Top ring 220 and bottom ring 222 apply force to the anatomy of the patient to neutralize the forces exerted by tissue surrounding the underlying artery. Because rings 220 and 222 are both compressible, the height of sidewall 184 decreases as sidewall 184 is pressed against the patient. As a result, diaphragm 186 is also compressed. However, because intermediate portion 235 of upper diaphragm sheet 230 is permitted to move upward into expansion cavity 214, interface chamber 242 partially defined by diaphragm 186 does not experience a large volume decrease and a corresponding large pressure increase. Thus, sidewall 184 is able to apply a greater force to the anatomy of the patient without causing a corresponding large, error producing increase in pressure within interface chamber 242 due to the change in height of sidewall 184 and the change in shape of diaphragm 186.

At the same time, sensor 180 permits accurate and consistent calculation of blood pressure. Because sidewall 184, diaphragm 186 and fluid coupling medium 188 of sensor 180 form a large sensing area through which blood pressure pulses may be transmitted to transducer 66, sensor 180 is not as dependent upon accurate positioning of transducer 66 over the underlying artery. Thus, sensor 180 is more tolerant to patient movement as measurements are being taken.

Moreover, sensor 180 achieves a zero pressure gradient across the active face or portion 240 of the sensor, achieves a zero pressure gradient between the transducer and the underlying artery, attenuates or dampens pressure pulses that are parallel to the sensing surface of the sensor, and neutralizes forces of the tissue surrounding the underlying artery. Sensor 180 contacts and applies force to the anatomy of the patient across skirt 238 and active portion 240. However, the pressure within interface chamber 242 is substantially equal to the pressure applied across active portion 240. The remaining force applied by sensor 180 across skirt 238 which neutralizes or offsets forces exerted by the tissue surrounding the underlying artery is transferred through sidewall 184 to top 192. As a result, the geometry and construction of sensor 180 provides the proper ratio of pressures between skirt 238 and active portion 240 to neutralize tissue surrounding the underlying artery and to accurately measure the blood pressure of the artery. In addition, because fluid coupling medium 188 within interface chamber 242 is isolated from sidewall 184, pressure pulses parallel to the underlying artery, forces from tissue surrounding the underlying artery and other forces absorbed by sidewall 184 are not transmitted through fluid coupling medium 188 to transducer 66. Consequently, sensor 180 also achieves a zero pressure gradient between transducer 66 and the underlying artery.

Although the present invention has been described with reference to preferred embodiments, workers skilled in the art will recognize that changes may be made in form and detail without departing from the spirit and scope of the invention.

What is claimed is:

1. A sensor for sensing blood pressure within an underlying artery of a patient, the sensor comprising:
   a pressure transducer for sensing blood pressure pulses of the underlying artery, the transducer having a sensing surface;
   a flexible diaphragm having an active portion for transmitting blood pressure pulses of the underlying artery;
   interface means coupled between the sensing surface of the transducer and the flexible diaphragm for transmitting the blood pressure pulses within the underlying artery from the flexible diaphragm to the sensing surface of the transducer; and
   means isolated from the interface means and surrounding the active portion for conforming to the anatomy surrounding the underlying artery.

2. The sensor of claim 1 wherein the means for conforming includes means for equalizing pressure around the active portion.

3. The sensor of claim 2 wherein the means for equalizing pressure includes a compressible ring surrounding the active portion having a top surface and a bottom surface, the ring being partially filled with a fluid so that the distance between the top surface and the bottom surface varies along the ring to conform to the anatomy of the patient surrounding the underlying artery.

4. The sensor of claim 3 including:
   a foam rubber ring surrounding the active portion and positioned between the compressible ring and the anatomy of the patient.

5. The sensor of claim 1 including means isolated from the interface means and at least partially surrounding the active portion for dampening forces in a direction parallel to the underlying artery which are exerted by the blood pressure pulses on the sensor so that a substantially zero pressure gradient exists within the interface means across the pressure transducer.

6. The sensor of claim 5 wherein the means for dampening includes a compressible sidewall surrounding the active portion.

7. The sensor of claim 1 wherein the tissue surrounding the underlying artery exerts a force as the underlying artery is compressed, and wherein the sensor includes means isolated from the interface means and surrounding the active portion for neutralizing the force exerted by the tissue surrounding the underlying artery.

8. The sensor of claim 7 wherein means for neutralizing includes a compressible sidewall surrounding the active portion.

9. A sensor for sensing blood pressure within an underlying artery, the sensor comprising:
   a pressure transducer for sensing blood pressure pulses of the underlying artery, the transducer having a sensing surface;
   a flexible diaphragm spaced from the sensing surface, the flexible diaphragm having an active portion for receiving forces exerted by the blood pressure pulses;
   interface means coupled between the sensing surface of the transducer and the flexible diaphragm for transmitting the blood pressure pulses within the underlying artery from the flexible diaphragm to the sensing surface of the transducer; and
   means isolated from the interface means and at least partially surrounding the active portion for dampening forces in a direction parallel to the underlying artery which are exerted by the blood pressure pulses on the sensor so that a substantially zero pressure gradient exists across the active portion of the flexible diaphragm.

10. A sensor for measuring blood pressure pulses within an underlying artery surrounded by tissue as the underlying artery is compressed, wherein the tissue surrounding the underlying artery exerts a force as the underlying artery is compressed, the sensor comprising:
- a pressure transducer for sensing blood pressure pulses of the underlying artery, the transducer having a sensing surface;
- a flexible diaphragm spaced from the sensing surface, the diaphragm having an active portion for receiving forces exerted by the blood pressure pulses;
- interface means coupled between the sensing surface of the transducer and the flexible diaphragm for transmitting the blood pressure pulses within the underlying artery from the flexible diaphragm to the sensing surface of the transducer; and
- means isolated from the interface means and surrounding the active portion for neutralizing the force exerted by the tissue surrounding the underlying artery.

11. A sensor for sensing blood pressure within an underlying artery, the sensor comprising:
- a pressure transducer for sensing blood pressure pulses of the underlying artery, the transducer having a sensing surface;
- supporting means for supporting the transducer above the underlying artery;
- a flexible diaphragm spaced from the sensing surface; and
- interface means coupled between the sensing surface of the transducer and the flexible diaphragm for transmitting the blood pressure pulses within the underlying artery from the flexible diaphragm to the sensing surface of the transducer, wherein the interface means are isolated from the supporting means.

12. The sensor of claim 11 wherein the interface means comprises a fluid coupling medium and wherein the flexible diaphragm partially defines an interface chamber extending between the flexible diaphragm and the sensing surface of the transducer, the interface chamber containing the fluid coupling medium and being substantially isolated from the supporting means so as to prevent pressure from the support means from being transmitted to the fluid coupling medium and to the sensing surface of the transducer.

13. The sensor of claim 12 wherein the flexible diaphragm includes:
- a first flexible member having an active portion encircled by the supporting means, wherein the active portion receives forces exerted by the blood pressure pulses; and
- a second flexible member supported between the supporting means and the first flexible member and bonded to the first flexible member, the second flexible member having a portion above the active portion which is isolated from the supporting means so that the isolated portion of the second flexible member and the active portion of the first flexible member at least partially define the interface chamber.

14. The sensor of claim 13 wherein the supporting means defines an expansion cavity so that the isolated portion of the second flexible member is permitted to move into the expansion cavity without changing the volume of the interface chamber when the sensor is conforming to the anatomy of the patient surrounding the underlying artery.

15. The sensor of claim 12 wherein the means for supporting includes a compressible sidewall at least partially surrounding the sensing surface of the transducer.

16. The sensor of claim 15 wherein the compressible sidewall includes:
- a fluid filled wall for conforming to the anatomy surrounding the underlying artery, the fluid filled wall equalizing pressure around the sensing surface of the transducer.

17. The sensor of claim 15 wherein the compressible sidewall includes:
- a foam wall for dampening forces in a direction parallel to the underlying artery which are exerted by the blood pressure pulses on the sensor so that a substantially zero pressure gradient exists within the interface means across the pressure transducer.

18. The sensor of claim 15 wherein the tissue surrounding the underlying artery exerts a force as the underlying artery is compressed and wherein the compressible sidewall includes:
- a foam wall for neutralizing the force exerted by the tissue surrounding the underlying artery.

19. A sensor for sensing blood pressure within an underlying artery, the sensor comprising:
- a pressure transducer for sensing blood pressure pulses of the underlying artery, the transducer having a sensing surface;
- a flexible diaphragm spaced from the sensing surface;
- a sidewall coupled to the transducer, wherein the sidewall supports the transducer above the underlying artery; and
- a fluid coupling medium coupled between the sensing surface of the transducer and the flexible diaphragm and isolated from the sidewall so that blood pressure pulses within the underlying artery are transmitted from the flexible diaphragm to the sensing surface of the transducer and so that external forces from the sidewall are not transmitted through the fluid coupling medium to the sensing surface of the transducer.

20. A sensor or claim 19 wherein the flexible diaphragm at least partially defines an interface chamber isolated from the sidewall and wherein the interface chamber contains the fluid coupling medium.

21. A sensor for sensing blood pressure within an underlying artery of a patient, the sensor comprising:
- a pressure transducer for sensing blood pressure pulses of the underlying artery, the transducer having a sensing surface;
- a flexible diaphragm spaced from the sensing surface, wherein the flexible diaphragm at least partially defines an interface chamber in communication with the sensing surface of the pressure transducer;
- a fluid coupling medium within the interface chamber for transmitting blood pressure pulses within the underlying artery from the flexible diaphragm to the sensing surface of the transducer; and
- a supporting structure for supporting the transducer above the underlying artery, wherein the supporting structure defines an expansion cavity adjacent the flexible diaphragm so that the interface chamber containing the fluid coupling medium may undergo a change in shape without a corresponding change in volume and pressure.

* * * * *

UNITED STATES PATENT AND TRADEMARK OFFICE
CERTIFICATE OF CORRECTION

PATENT NO. : 5,450,852

DATED : September 19, 1995

INVENTOR(S) : G. KENT ARCHIBALD, TIMOTHY G. CURRAN, ORLAND H. DANIELSON, MARIUS O. POLIAC, ROGER C. THEDE

It is certified that error appears in the above-indentified patent and that said Letters Patent is hereby corrected as shown below:

Col. 18, line 42, delete "A sensor or claim 19", and insert --The Sensor of claim 19--

Signed and Sealed this

Second Day of January, 1996

Attest:

BRUCE LEHMAN

Attesting Officer

Commissioner of Patents and Trademarks